(12) United States Patent
Turner

(10) Patent No.: US 8,887,919 B2
(45) Date of Patent: Nov. 18, 2014

(54) NASAL CANNULA COVER

(76) Inventor: Charles Andrew Turner, Orefield, PA (US)

( * ) Notice: Subject to any disclaimer, the term of this patent is extended or adjusted under 35 U.S.C. 154(b) by 1233 days.

(21) Appl. No.: 12/126,293

(22) Filed: May 23, 2008

(65) Prior Publication Data

US 2009/0292258 A1 Nov. 26, 2009

(51) Int. Cl.
*B65D 69/00* (2006.01)
*A62B 7/00* (2006.01)
*A61M 16/06* (2006.01)

(52) U.S. Cl.
CPC ....... *A61M 16/0666* (2013.01); *A61M 2209/06* (2013.01); *A61M 2205/11* (2013.01)
USPC ..................... 206/570; 128/207.18

(58) Field of Classification Search
USPC .............. 128/207.18; 604/263; 206/570, 210, 206/5.1, 6.1, 363, 364, 438, 439, 485; D3/203.1
IPC ......................................................... A61B 19/02
See application file for complete search history.

(56) References Cited

U.S. PATENT DOCUMENTS

| | | | | | |
|---|---|---|---|---|---|
| 4,007,740 | A | * | 2/1977 | Owen ........................... | 604/192 |
| 4,083,368 | A | | 4/1978 | Freezer | |
| 4,332,322 | A | * | 6/1982 | Jaeschke et al. ............. | 206/364 |
| 4,551,138 | A | * | 11/1985 | Shinohara .................... | 604/262 |
| 5,437,267 | A | | 8/1995 | Weinstein | |
| 6,012,580 | A | * | 1/2000 | Peters et al. .................. | 206/470 |
| 6,026,811 | A | | 2/2000 | Settle | |
| D427,425 | S | * | 7/2000 | St.ang.hl ..................... | D3/203.1 |
| 6,173,868 | B1 | | 1/2001 | DeJonge | |
| 6,305,591 | B1 | * | 10/2001 | Jones ............................ | 224/601 |
| D458,127 | S | * | 6/2002 | de Groote ..................... | D9/423 |
| 6,494,204 | B1 | | 12/2002 | Ponce | |
| 6,711,847 | B1 | * | 3/2004 | Udelhoven .................... | 43/25.2 |
| 6,719,737 | B2 | * | 4/2004 | Kobayashi .................... | 604/263 |
| D496,154 | S | * | 9/2004 | Herman et al. ............. | D3/203.1 |
| D548,954 | S | * | 8/2007 | Andersen et al. ............ | D3/203.1 |
| D569,608 | S | * | 5/2008 | Rowe .......................... | D3/203.1 |
| D612,148 | S | * | 3/2010 | Treece et al. ................ | D3/203.1 |
| D614,048 | S | * | 4/2010 | Smith .......................... | D3/203.1 |
| 7,798,332 | B1 | * | 9/2010 | Brunet ......................... | 206/570 |
| D625,913 | S | * | 10/2010 | Phillips ........................ | D3/205 |
| 2003/0159968 | A1 | * | 8/2003 | McMichael et al. .......... | 206/570 |
| 2005/0218022 | A1 | * | 10/2005 | Cervantes ..................... | 206/363 |
| 2005/0236001 | A1 | * | 10/2005 | Williams .................. | 128/207.18 |
| 2005/0279649 | A1 | * | 12/2005 | Thacker ....................... | 206/63.5 |
| 2006/0138157 | A1 | * | 6/2006 | Timm et al. .................. | 220/839 |
| 2007/0270736 | A1 | | 11/2007 | Giarrocco-Brettner | |
| 2008/0023472 | A1 | * | 1/2008 | Brandt ......................... | 220/4.23 |
| 2008/0249475 | A1 | * | 10/2008 | Albrecht et al. ......... | 604/167.06 |
| 2008/0255526 | A1 | * | 10/2008 | Bosse et al. .................. | 604/263 |
| 2008/0292123 | A1 | * | 11/2008 | Jensen ......................... | 381/322 |
| 2009/0084703 | A1 | * | 4/2009 | Eskenazi et al. ............. | 206/594 |
| 2009/0188831 | A1 | * | 7/2009 | Blackman .................... | 206/531 |
| 2009/0199858 | A1 | | 8/2009 | Hagberg et al. | |
| 2009/0223851 | A1 | * | 9/2009 | Jacobs et al. ................. | 206/438 |
| 2010/0147302 | A1 | * | 6/2010 | Selvarajan et al. ...... | 128/204.23 |

FOREIGN PATENT DOCUMENTS

CH 699918 B1 * 5/2010

* cited by examiner

*Primary Examiner* — Loan H Thanh
*Assistant Examiner* — Sundhara Ganesan

(57) ABSTRACT

The present invention is a protective cover for a nasal cannula. The device completely encloses the two prongs of the nasal cannula when properly installed. This protective cover will keep the nasal cannula from contacting potentially unclean surfaces when the nasal cannula is not in use.

21 Claims, 4 Drawing Sheets

Figure 2A:
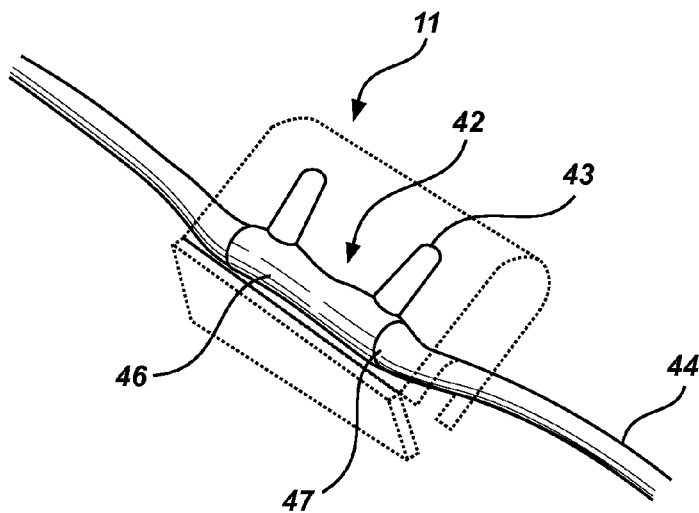

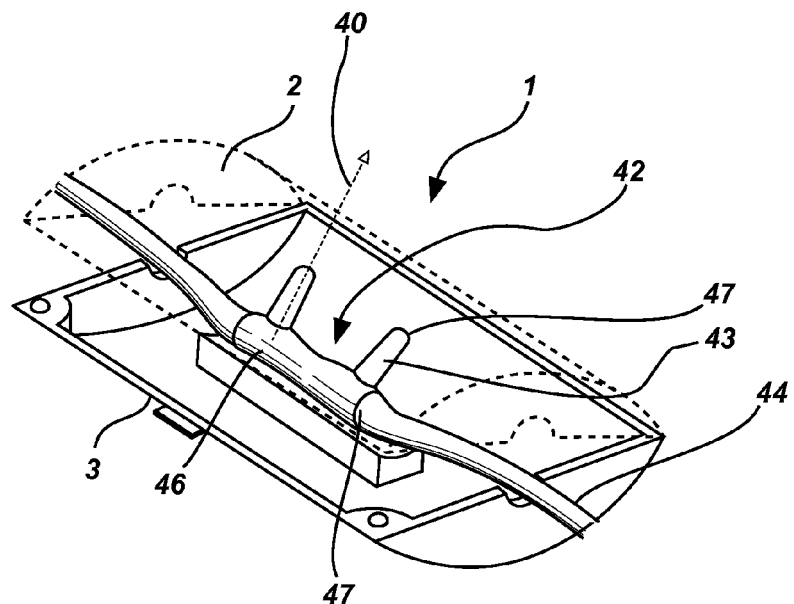
Fig. 1a
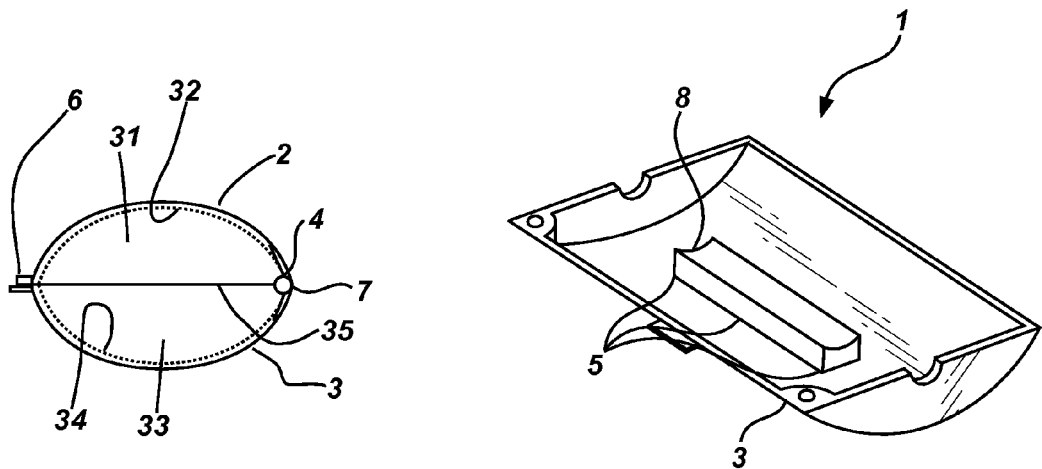
Fig. 1b  Fig. 1c

NASAL CANNULA COVER

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The field of the present invention is delivery systems for patients taking oxygen or other fluids or gases through a nasal cannula. More specifically, the field of the present invention is protective storage of the nasal cannula while not in use.

2. Description of Related Art

It is known that a nasal cannula is a device used to deliver supplemental oxygen to a person through the nostrils. This device consists of a plastic tube, connected to an oxygen source, and a set of two prongs which engage the nostrils of the wearer. Oxygen is delivered through holes in the prongs. The tubing is kept in place by fitting it around the patient's ears.

Nasal cannulas are manufactured and transported in clean conditions so as to keep the area of the prongs clean. Standard operating procedure among medical professionals dictates that when a nasal cannula comes in contact with any unclean or unsanitary surface, it must be discarded It is also known that to keep the nasal cannula from becoming soiled when not in use, the wearer or caregiver will typically hang it on a bed post or hook. Unfortunately, the natural coiling and uncoiling properties of the plastic tube can cause it to fall even when it appears to be safely secured.

A number of accessory devices for use with nasal cannulas have been proposed. By way of example, Published U.S. Patent Application 2007/0270736 to Giarrocco-Brettner shows a bulb syringe improvement. The device partially covers a nasally inserted portion of the bulb syringe. In addition, it prevents contact between the nasally inserted portion of the bulb syringe and an unclean table surface. The device does not, however, provide full coverage over a two prong nasal cannula.

In addition, a number of other accessories for nasal cannulas are shown in the art. For example, U.S. Pat. No. 6,026,811 to Settle shows a protective cover for the tubing of a nasal cannula which provides comfort for the patients ear. Published U.S. Patent Application 2005/0236001 to Williams shows a bridle system which clamps around the tubes exiting a patient's nose. However, the prior art does not show a cover for use in protecting the nasal cannula. What is needed is a device that protects a nasal cannula from becoming soiled while not use.

BRIEF SUMMARY OF THE INVENTION

The present invention is a protective cover for a nasal cannula. The device completely encloses the two prongs of the nasal cannula when properly installed. This protective cover will keep the nasal cannula from contacting the floor, bed sheets, or other potentially unclean surfaces when the nasal cannula is not in use. Multiple embodiments are described. Generally, the device consists of two components which are pivotally attached together. The hinge can be of any type, for instance, a living hinge or a pinned hinge, and optionally the two halves may be biased toward each other or away from each other, for instance, by a spring.

In a first embodiment, the two halves are substantially similar to each other, and both are clamshell shaped. The interior of the clamshell shaped covers contain a fixturing rib for contacting the two sides of the nasal cannula base tube. In operation, the patient need only place the cannula base tube on the fixturing rib of the bottom cover half. The patient can then close the other cover, which will secure the cannula base tube without contacting the cone shaped prongs—which are the nasally inserted portions.

In a second embodiment, the first half is elongated to match the side profile shape of the nasal cannula. The patient need only insert the cone shaped prongs into the first half. The first half has a base tube opening with half moon shaped clips. The half moon shaped clips attach to the cannula base tube. Finally, a hinge attached door is closed to seal the nasal cannula.

In a third embodiment, the cover is comprised of two shells which when closed form an interior cylinder. When closed around the nasal cannula, the cover may rotate 360 degrees around the axis of the cannula base tube. While rotating the cover, no part of the nasally inserted cannula can touch any part of the interior cylinder. In addition, the barrel cover contains two feed tube locators which abut against the cannula feed tube shoulder, and prevent lateral sliding of the barrel cover.

All embodiments of the present invention can include leg protrusions which provide stability against rolling on horizontal surfaces.

There has thus been outlined the more important features of the invention in order that the detailed description thereof that follows may be better understood, and in order that the present contribution to the art may be better appreciated. There are additional features of the invention that will be described hereinafter and which will form the subject matter of the claims appended hereto. In as much as the foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent methods and structures do not depart from the spirit and scope of the invention as set forth in the appended claims.

Therefore, it is an object of the present invention to provide a nasal cannula cover which prevents the nasal cannula from contacting potentially unclean surfaces when properly installed.

Yet another object of the present invention to provide a nasal cannula cover which is lightweight, durable and inexpensive to manufacture.

It is a further object of the present invention to provide a nasal cannula cover that is maintained in a position for easy access by the user or health professional when not installed over the prongs of the cannula.

It is a further object of the invention to provide a cannula cover that is easy for the patient or health professional to install and remove from the prongs of the cannula.

It is a further object of the present invention to provide a cannula cover with interior surfaces that will not contact un-clean surfaces while in the un-installed state.

BRIEF DESCRIPTION OF THE SEVERAL VIEWS OF THE DRAWING(S)

Various other objects, features and attendant advantages of the present invention will become fully appreciated through consideration of the accompanying drawings and the detailed description following, in which like reference characters designate the same or similar parts throughout the several views, and wherein:

FIG. 1a-c shows a clamshell cover. FIG. 1a is a top perspective view of the clamshell cover with the nasal cannula in place. FIG. 1b is a side view of the clamshell cover. FIG. 1c is a top perspective view of the bottom shell of the clamshell cover.

Figure 2B:
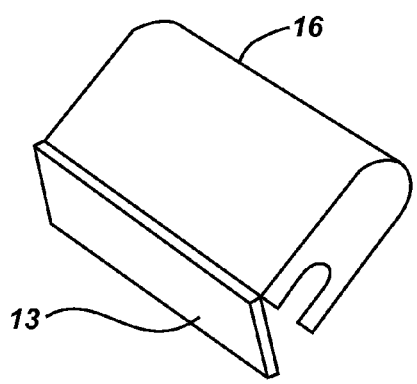
Figure 2C:
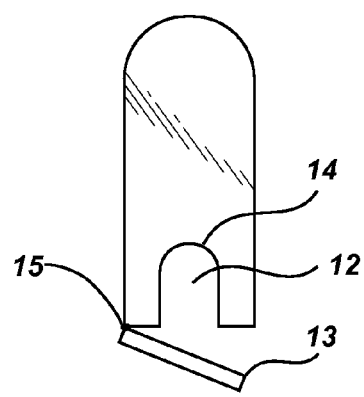

FIG. 2a-c shows a reusable slide-on cover. FIG. 2a shows a top perspective view of the reusable slide-on cover with the nasal cannula in place. FIG. 2b shows a top perspective view of the reusable slide-on cover. FIG. 2c shows a side view of the reusable slide-on cover.

Figure 3A:
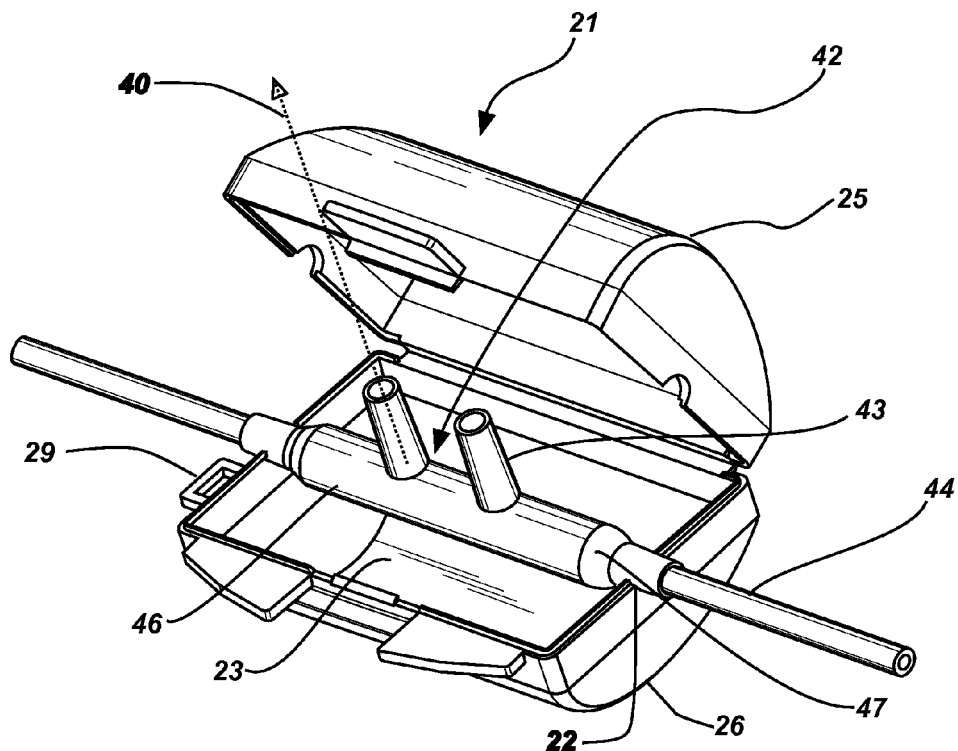
Figure 3B:
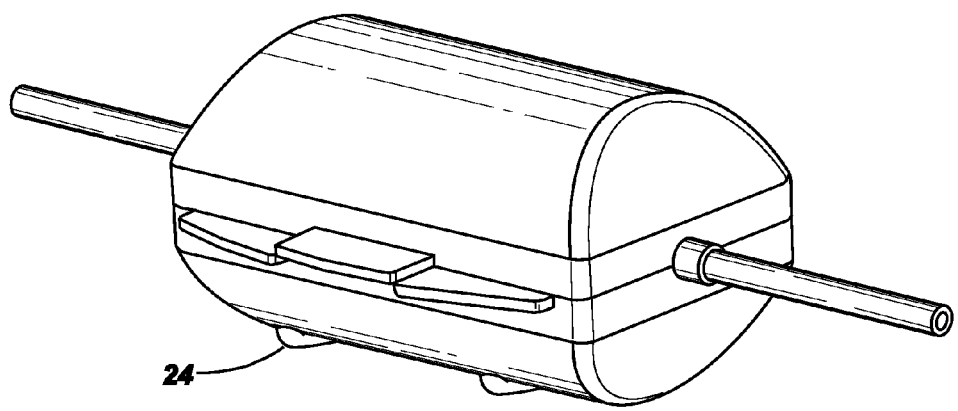

FIG. 3a-b shows a barrel cover. FIG. 3a shows a top perspective view of the barrel cover with the top shell open and the nasal cannula in place. FIG. 3b shows a top perspective view of the barrel cover with the top shell mated with the bottom shell.

Figure 4:
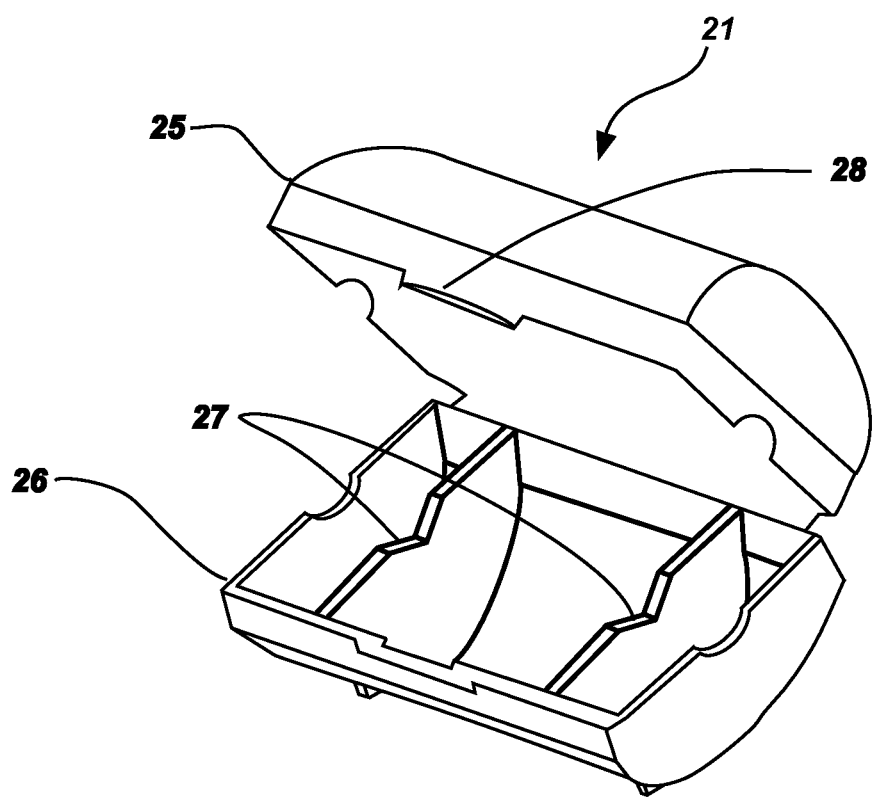

FIG. 4 shows a top perspective view of the barrel cover with several additions.

DETAILED DESCRIPTION OF THE INVENTION

Referring now to the first embodiment of the present invention in FIG. 1a-c, a clamshell cover 1, or a cover, is shown. A nasal cannula 42 is composed of a cannula base tube 46, and one or more cannula feed tube 44, and one or more cone shaped prong 43. For reference, an axis of the distal end of the cannula 40 is defined as the central longitudinal axis of the cone shaped prong 43. Also, the cone shaped prong 43 has a distal end 47. The clamshell cover 1 includes a top cover component 2 and a bottom cover component 3. The top cover component 2 has a first opening 31 in a bottom surface 32, and the bottom cover component 3 has a second opening 33 in a top surface 34. The top cover component 2 can contact the bottom cover component 3 at a mating 35.

The top cover component 2 is attached to the bottom cover component 3 by a hinge 7, or connecting member, which among other alternatives, can be of the known living hinge or pinned hinge types. Referring to FIG. 1b, the top cover component 2 is urged into contact with the bottom cover component 3 by a torsion spring 4, or biasing member. When in the closed position seen in FIG. 1b, a latch 6, or holding member, holds the top cover component 2 in contact with bottom cover component 3. As seen in FIG. 1c, the bottom cover component 3 has one or more base tube supports 5, or suspending member. The base tube support 5 contacts the cannula base tube 46 of the nasal cannula 42 when the nasal cannula 42 is inside the clamshell cover 1. As seen, the base tube support 5 has a semi-circular prong top 8 which conforms to the shape of the cannula base tube 46. In addition, the base tube support 5 is attached to both the top cover component 2 and the bottom cover component 3, which provides for two contact surfaces on the cannula base tube 46.

Referring now to FIG. 2a-c, the second embodiment of the present invention is shown. A reusable slide-on cover 11 is composed of a top cover 16 and a hinged closure 13. Both the top cover 16 and the hinged closure 13 are made of semi-rigid plastic material. The top cover 16 has a base tube opening 12 which slides over the cannula feed tube 44. When covering the nasal cannula 42, a half moon shaped clip 14 contacts the cannula feed tube 44 such that light manual force is required to press the reusable slide-on cover 11 over the cannula feed tube 44. The hinged closure 13 pivots freely on a closure hinge 15. Once the half moon shaped clip 14 engages the cannula feed tube 44, the patient 45 can manually rotate the hinged closure 13 to cover the base tube opening 12.

Referring now to FIG. 3a-b and FIG. 4, the third embodiment of the present invention is shown. As seen in FIG. 3a, a barrel cover 21 is comprised of a top half 25 and a bottom half 26. When the top half 25 and the bottom half 26 are mated together, the interior space forms an inner cylinder 23, or interior space, which provides clearance between the inner cylinder 23 and the cone shaped prong 43. The barrel cover 21 can rotate 360 degrees around the longitudinal axis of the cannula base tube 46, and the clearance between the cone shaped prong 43 and the inner cylinder 23 will remain. The barrel cover 21 also has a feed tube locator 22 on two sides of the bottom half 26. The feed tube locator 22 contacts the cannula base tube 46 on the nasal cannula 42. The feed tube locator 22 prevents lateral sliding in either direction along the longitudinal axis of the cannula base tube 46. A tether attachment 29 releasably attaches tether members, which are elongated flaccid components that hang the barrel cover at various locations. The tether members can include various quick attachment devices including hooks, snaps, hook & loop, or buttons. Referring now to FIG. 3b, the barrel cover 21 has one or more leg protrusion 24, or stabilizing member, which provide for setting barrel cover 21 on horizontal surfaces without freely rolling.

Referring now to FIG. 4, the third embodiment of the present invention is shown with additional features. The barrel cover 21 can also have a base tube locator 27, or guidance member, on two sides of the bottom half 26. In addition, base tube locator 27 can be added to the top half 25. The base tube locator 27 has a V-shape which contacts the cannula base tube 46 on the nasal cannula 42. The base tube locator 27 allows misalignment of the nasal cannula 42 to be corrected as the top half 25 approaches the bottom half 26. In addition, FIG. 4 shows a press to open latch 28, or actuating member. The press to open latch 28 is actuated by compressing the top half 25 with light finger force.

It is to be understood that the invention is not limited in its application to the details of construction and to the arrangements of the components set forth in the preceding description or illustrated in the drawings. The invention is capable of other embodiments and of being practiced and carried out in various ways. Also, it is to be understood that the phraseology and terminology employed herein are for the purpose of the description and should not be regarded as limiting.

The invention claimed is:

1. A cover that protects two fluid delivery prongs of a nasal cannula that dispenses fluids into a body at two nasal locations, comprising:

a first opening in a bottom surface of a top cover component, the top cover component formed as a solid, continuous exterior surface;
a top surface of a bottom cover component, the bottom cover component formed as a solid, continuous exterior surface; and
a base tube opening disposed on opposing sides of at least one of the top cover component and the bottom cover component, the base tube opening permitting tubing of the nasal cannula to extend therethrough when the cover is closed;
wherein upon mating the first opening and the top surface, an interior space is formed between the top cover component and the bottom cover component that is of sufficient volume to enclose the two fluid delivery prongs of the nasal cannula after the nasal cannula is removed from the two nasal body orifice, where no part of the two fluid delivery prongs of the nasal cannula touch any part of the interior space; and
wherein the entire bottom surface of the top cover component mates with and contacts the top surface of the bottom cover component.

2. The cover of claim 1, wherein:
a mating of the first opening in the bottom surface of the top cover component and the top surface of the bottom cover component lie in a plane that is essentially parallel to the axis of the two fluid delivery prongs of the nasal cannula.

3. The cover of claim 1, wherein
a mating of the first opening in the bottom surface of the top cover component and the top surface of the bottom cover component lie in a plane that is essentially orthogonal to the axis of the two fluid delivery prongs of the nasal cannula.

4. The cover of claim 1, wherein:
a mating of the first opening in the bottom surface of the top cover component and the top surface of the bottom cover component lie in a plane that is essentially at an oblique angle to the axis of the two fluid delivery prongs of the nasal cannula.

5. The cover of claim 1, further comprising:
a holding member that acts on the top cover component and the bottom cover component to hold the top cover component and the bottom cover component.

6. The cover of claim 1, further comprising:
one or more suspending members that prevent a portion of the nasal cannula from contacting the top cover component or the bottom cover component.

7. The cover of claim 1, further comprising:
one or more contours in the bottom surface of the top cover component or the top surface of the bottom cover component allowing the cover to move without interference from the nasal cannula.

8. The cover of claim 1, further comprising:
one or more tether members that connect the top cover component or bottom cover component to one or more cannula components.

9. The cover of claim 1, further comprising:
a connecting member that connects the top cover component to the bottom cover component, wherein the connecting component allows relative motion between the top cover component and the bottom cover component between at least one position where the top cover component and the bottom cover component are separated sufficiently for the nasal cannula to pass therebetween and a second position where the top cover component and the bottom component mate to contain the nasal cannula in the space therebetween.

10. The cover of claim 9, wherein:
a mating of the first opening in the bottom surface of the top cover component and the top surface of the bottom cover component lie in a plane that is essentially parallel to the axis of the two fluid delivery prongs of the nasal cannula.

11. The cover of claim 9, wherein:
a mating of the first opening in the bottom surface of the top cover component and the top surface of the bottom cover component lie in a plane that is essentially orthogonal to the axis of the two fluid delivery prongs of the nasal cannula.

12. The cover of claim 9, wherein:
a mating of the first opening in the bottom surface of the top cover component and the top surface of the bottom cover component lie in a plane that is essentially at an oblique angle to the axis of the two fluid delivery prongs of the nasal cannula.

13. The cover of claim 9, further comprising:
a holding member that acts on the top cover component and the bottom cover component to hold the top cover component and the bottom cover component in the second position.

14. The cover of claim 9, further comprising:
one or more suspending members that prevent a portion of the one or more cannulas from contacting the top cover component or the bottom cover component when the top cover component and bottom cover component are in the second position.

15. The cover of claim 9, further comprising:
one or more contours in the bottom surface of the top cover component or the top surface of the bottom cover component allowing the surfaces to move into the second position without interference from cannula assembly components.

16. The cover of claim 9, further comprising:
one or more tether members that connect the top cover component or bottom cover component to one or more cannula components, wherein the one or more tether members are releasable attachment devices selected from the group consisting of hooks, snaps, hook & loop, and buttons.

17. The cover of claim 9, wherein:
the connecting member that connects the top cover component to the bottom cover component confines the relative motion of the top cover component and the bottom cover component to a pivoting motion.

18. The cover of claim 9, further comprising:
a biasing member that acts on the top cover component and the bottom cover component in a direction towards the second position.

19. The cover of claim 9, further comprising:
one or more actuating members that, when depressed, move the top cover component and the bottom cover component toward the second position from the first position when depressed by an inferred patient.

20. The cover of claim 9, further comprising:
one or more stabilizing members attached to the top cover component or the bottom cover component that provide substantially flat surfaces, wherein the substantially flat surfaces contact a horizontal surface and inhibit rolling on the horizontal surface.

21. The cover of claim 9, further comprising:
one or more cannula guidance members attached to the top cover component or the bottom cover component that provide to alignment to the nasal cannula as the top cover component approaches the bottom cover component.

\* \* \* \* \*